United States Patent [19]
Unger et al.

[11] Patent Number: 5,824,312
[45] Date of Patent: Oct. 20, 1998

[54] SUNSCREEN AGENTS FROM NATURAL SOURCES

[75] Inventors: Evan C. Unger; Thomas P. Mc Creery, both of Tucson, Ariz.

[73] Assignee: ImaRx Pharmaceutical Corp., Tucson, Ariz.

[21] Appl. No.: 573,590

[22] Filed: Dec. 15, 1995

Related U.S. Application Data

[63] Continuation of Ser. No. 209,531, Mar. 10, 1994, abandoned.
[51] Int. Cl.⁶ .............................. A61K 35/78; A61K 7/40; A61K 7/42
[52] U.S. Cl. ...................... 424/195.1; 514/783; 424/59; 424/60; 424/70.9
[58] Field of Search ................................... 424/195.1, 59, 424/60, 70.9, 78.3; 514/783, 844

[56] References Cited

FOREIGN PATENT DOCUMENTS 05163115   6/1993   Japan .

OTHER PUBLICATIONS

Braun, et al., "Regulation Of UV–Protective Pigment Synthesis In the Epidermal Layer of Rye Seedlings", *Photochemistry and Photobiology*, vol. 57(2), (1993) pp. 318–323.
Lowe, et al., "Indoor And outdoor Efficacy Testing Of A Broad–Spectrum Sunscreen Against Ultraviolet A Radiation In Psoralen–Sensitized Subjects", *J. Amer. Acad.*, (Aug. 1987), vol. 17, No. 2, Part 1, pp. 224–230.

*Primary Examiner*—John Kight
*Assistant Examiner*—Howard C. Lee
*Attorney, Agent, or Firm*—Woodcock Washburn Kurtz Mackiewicz & Norris LLP

[57] ABSTRACT

Photoabsorptive compounds are disclosed which comprise a purified extract of a plant or plant part, wherein said plant is indigenous to an arid region of the world, especially where said arid region is located between 35° north latitude and 35° south latitude. The photoabsorptive compounds in many cases are capable of absorbing solar radiation from about 190 nm to about 500 nm, comprising ultraviolet A, ultraviolet B, and high energy visible light. In particular embodiments, the plant part is pollen, and the plant is mesquite, *Prosopis juliflora;* Mexican palo verde, *Parkinsonia aculeata;* blue palo verde, *Cercidium floridum;* or foothills palo verde, *Cercidium microphyllum.*

18 Claims, No Drawings

SUNSCREEN AGENTS FROM NATURAL SOURCES

This is a continuation of application Ser. No. 08/209,531, filed Mar. 10, 1994, now abandoned.

BACKGROUND OF THE INVENTION

1. Field of the Invention

This invention relates to the field of sunscreen agents, which are substances such as p-aminobenzoic acid (PABA) and benzophenones used in suntan preparations to protect the human skin from excessive ultraviolet radiation. Sunscreen agents are chemical or physical substances which block or absorb ultraviolet radiation before it can be absorbed by chromophores in the skin. Because ultraviolet radiation can also cause significant damage to various man-made materials used in any number of structural and other applications, such as various polymers and paints of all descriptions, sunscreen agents also find applications in protecting such materials from ultraviolet radiation. The field of the present invention thus also extends to these areas of interest as well.

Ultraviolet radiation is, of course, only a part of the overall spectrum of electromagnetic radiation which the earth's surface, and therefore, human skin receives from the sun. Of particular interest in this solar spectrum, for their potential impact on the health of the human organism, and especially the skin, are the ultraviolet, visible and infrared regions. Solar radiation, largely in the ultraviolet region, has adverse short- and long-term effects on the various layers of the human skin. Sunburn, and its resultant inflammation, is predominantly caused by ultraviolet B radiation (UVB), while both UVB and UVA probably contribute to aging and to skin cancer. Ultraviolet radiation is thus of particular interest because of its established role in oncogenesis, i.e., in the genesis of skin cancers such as malignant melanoma.

Consequently, there has always been an interest in the use of sunscreen agents to protect the skin from sunburn, as well as more serious effects such as aging and the development of skin cancer. Indeed, effective sunscreens are of even greater importance at the present time because of the recent decrease in the extent of the earth's protective ozone layer and the concomitant rise in incident ultraviolet radiation striking the earth's surface. This is of crucial importance not only for the prevention of skin cancers, but also for reducing or preventing the degradation of man-made materials such as plastics and paints, which are exposed to that increased incident ultraviolet radiation. New and more effective sunscreens, i.e., ultraviolet absorbing compounds are, therefore, of great importance for human skin protection as well as for prolonging the useful life of paints, plastics and other man-made materials.

As already described, solar radiation causes the skin to age prematurely and increases the risk of skin cancer. Chronic sun exposure has been implicated as the primary causative factor in basal cell and squamous cell carcinoma of the skin. Severe sunburns are also a primary risk factor for the development of the deadliest of skin cancers, malignant melanoma.

In ultraviolet light the ultraviolet A (UVA) and ultraviolet B (UVB) spectrums are responsible for most of photocutaneous changes in the skin. Ultraviolet C (UVC) is generally absorbed by the ozone layer and is only generated by sources such as germicidal lamps and mercury arc lamps. The wavelength which marks the division between the ultraviolet B and ultraviolet A spectra is 320 nm, which is proximate to the upper wavelengths of ultraviolet B radiation that are the most erythemagenic, i.e., which cause abnormal redness of the skin. The ultraviolet A spectrum extends from 320 to 400 nm. Ultraviolet A is responsible for the pigment-darkening reaction which occurs within minutes of exposure, as well as the more delayed tanning reaction. Ultraviolet A can also evoke the sunburn reaction, but the erythemagenic capacity of ultraviolet A is much weaker than that of ultraviolet B.

The ultraviolet B spectrum, extending from 290 nm to 320 nm, is the most strongly erythemagenic portion of the ultraviolet spectrum, and is commonly designated as comprising "sunburn rays."

Formulations of sunscreens used heretofore have only included compounds which were effective in absorbing ultraviolet B radiation, and thus provided no protection against ultraviolet A radiation. While these sunscreens of the prior art are useful in many ways, there are several reasons why protection against ultraviolet A radiation is important as well, which thus provides an objective for sunscreen agents which the prior art has not recognized. Although the ultraviolet A spectrum is less energetic than the ultraviolet B spectrum, and is less erythemagenic, ultraviolet A radiation penetrates the skin more deeply than the B spectrum, and hence is capable of causing damage to the deeper portions of the skin tissue. Moreover, the advent of sunscreens which are only effective with respect to the ultraviolet B spectrum, has led to especially susceptible fair-skinned people spending more time in the sun, which in turn has increased their exposure to ultraviolet A radiation. Solar irradiance studies have shown that somewhere between 10 and 15 times as much ultraviolet A radiation as ultraviolet B radiation reaches the earth's surface each day. Furthermore, ultraviolet A radiation magnifies the damage to the skin caused by ultraviolet B radiation.

Although most damage to the skin is caused by ultraviolet radiation as described above, visible light with wavelengths in the range of 400 to 760 nm can induce reaction with porphyrins and dyes, and irradiation can heat the skin and cause skin damage such as erythema ab igne.

BRIEF DESCRIPTION OF THE PRIOR ART

In 1978 the Food and Drug Administration reclassified sunscreens as drugs designed to protect the structure and function of the skin. Category "1 Sunscreens", which have been judged by the FDA to be safe and effective, include twenty-one ultraviolet filters, fifteen of which are UVB absorbers and two of which are physical blockers. Sunblocks are physical agents that are opaque, and include, e.g., titanium dioxide, talc, and zinc oxide.

As already mentioned, aminobenzoic acid esters and benzophenones are commonly used, often in combination with cinnamates and salicylates. Butyl methoxydibenzoylmethane, used in combination with an ester of benzoic acid, has recently been shown to minimize the photochemical toxic response to UVA in psoralen-sensitized subjects; Lowe, N. J. et al., Indoor and outdoor efficacy testing of a broad spectrum sunscreen against ultraviolet A radiation in psoralen-sensitized subjects, *J. Amer. Acad. Dermatol.*, 1987, 17, 224–230. However, relatively few safe materials are available for absorbing UVA radiation.

Investigators have studied photoabsorptive compounds found exclusively in the epidermal layer of rye seedlings. These compounds have been identified as flavonoids. See Braun, J., and Tevini, M. (1993) Photochemistry and Photobiology, 57, 2, 318–323. However, no single compound has been identified which is capable of effectively absorbing both UVA and UVB radiation. Moreover, additional filters are needed to block the high energy visible spectrum (e.g.: 400 to 550 nm) which has also been shown to damage the skin.

SUMMARY OF THE INVENTION

The present invention is directed to one or more photoabsorptive compounds comprising a purified extract of a plant or plant part, wherein said plant is indigenous to an arid region of the world. Preferably, this arid region will be located between 35° north latitude and 35° south latitude. The present invention is directed to such photoabsorptive compounds capable of absorbing solar radiation in the ultraviolet B spectrum from about 290 nm to about 320 nm, and more broadly, from about 190 nm to about 500 nm, comprising ultraviolet A, ultraviolet B, and high energy visible light. The present invention is also directed to such photoabsorptive compounds wherein the plant part is the reproductive part of the plant, especially the flowering part and pollen of the plant, and wherein the plant is mesquite, *Prosopis juliflora;* Mexican palo verde, *Parkinsonia aculeata;* blue palo verde, *Cercidium floridum;* or foothills palo verde, *Cercidium microphyllum.*

The present invention is also directed to one or more photoabsorptive compounds produced by the process of extracting said compound(s) from a plant or plant part, and thereafter purifying said compound(s), wherein said plant is indigenous to an arid region of the world. Preferably, this arid region is located between 35° north latitude and 35° south latitude. The present invention is further directed to such photoabsorptive compounds wherein the step of extracting is carried out using an extracting agent selected from the group consisting of alkanols, especially methanol and ethanol; ketones, especially acetone; ethers, especially anisole; cycloalkanes, especially cyclohexane; alkanes and halogenated alkanes, especially hexane, dichloromethane and chloroform; aromatic hydrocarbons, especially benzene and toluene; and alkoxyalkylated ether polymers, especially methoxymethylated ether polymers such as glyme and diglyme.

The present invention also relates to a method of protecting the human skin from irritation or damage caused by impinging electromagnetic radiation in the ultraviolet B spectrum from about 290 nm to about 320 nm, and more broadly, from about 190 nm to about 500 nm, comprising ultraviolet A, ultraviolet B, and high energy visible light, comprising applying to said skin one or more photoabsorptive compounds comprising a purified extract of a plant or plant part, wherein said plant is indigenous to an arid region of the world, and preferably this arid region is located between 35° north latitude and 35° south latitude. The present invention still further relates to cosmetic formulations for application to the skin, including sunscreen formulations, moisturizing creams, and lip balms, containing a cosmetic excipient, and as an active ingredient, one or more photoabsorptive compounds comprising a purified extract of a plant or plant part, wherein said plant is indigenous to an arid region of the world, and preferably this arid region is located between 35° north latitude and 35° south latitude.

The present invention also relates to man-made materials protected from damage caused by impinging electromagnetic radiation from about 190 nm to about 500 nm, or any subdivisible subspectrum thereof, including ultraviolet A, ultraviolet B, and high energy visible light, wherein said materials contain an effective amount of one or more photoabsorptive compounds comprising a purified extract of a plant or plant part, wherein said plant is indigenous to an arid region of the world, and preferably this region is located between 35° north latitude and 35° south latitude.

The man-made materials protected from damage are especially those used in any number of structural and other applications where they are exposed to solar radiation, such as various polymers, synthetic resin and fiberglass laminates, and coating resins and paints of all descriptions. The present invention also relates to methods of providing such man-made materials which are protected from damage caused by impinging radiation, comprising adding thereto an effective amount of the photoabsorptive compound(s) of the present invention.

DETAILED DESCRIPTION OF THE INVENTION

The present invention, in its broadest and simplest form, is based on the discovery that there are naturally occurring compounds, produced by plants which are subject to extraordinary amounts of solar radiation, in order to protect especially sensitive parts thereof from damage by said solar radiation, said compounds having unique solar radiation absorbing properties. These compounds are produced by plants from arid regions of the world, which have thus experienced a high degree of natural selective pressure in evolutionary terms. The reproductive or flowering parts of such plants, including the pollen, are particularly susceptible to damage from solar radiation. Plants reproduce by combining their pollen, i.e., male sex cells or fertilizing grains of a flowering plant, with the ova, or female sex cells, of other plants of the same species to form seeds. Natural selection dictates that those plants will be the most successful in reproducing which have been best able to protect their flowering parts, and especially the pollen which they produce. The pollen contains genetic material called DNA which is especially susceptible to degradation by the photons comprising solar radiation, particularly intense solar radiation. It is hypothesized that for pollen produced during the summer months, compounds are generated by the plant as a constituent part of the pollen to guard against such solar radiation damage, since pollen granules are exposed directly to the sun. The DNA is relatively easily degraded by ultraviolet light.

This problem would be greatly exacerbated for plants growing in arid regions where the solar radiation is unrelieved by clouds for significantly long periods during the year. As used herein, the term "arid" means having insufficient rainfall to support agriculture, and in particular, less than 20 inches of rainfall per year on average, and more particularly, less than 5 inches of rainfall per year, on average. Included are those regions having prolonged dry spells, which may occur during any season of the year, and in which virtually no rainfall occurs for an extended period of time, even though during the remainder of the year, more substantial rainfall may be experienced.

This problem of exceptional amounts of solar radiation would be still further exacerbated for plants growing between 35° north latitude and 35° south latitude, where the solar radiation impinging on the earth is more intense than at other latitudes, and more penetrating due to the angle of incidence with the atmosphere. This additional qualification assists in further defining the plants which will be found to produce the compounds having unique solar radiation absorbing properties in accordance with the present invention.

Thus, it has been hypothesized that purified extracts derived from the flowering parts, especially the pollen of desert plants growing between 35° north latitude and 35° south latitude, such as the Sonoran and other desert areas of the southwestern United States, should contain effective photoabsorptive compounds.

In light of the discovery which constitutes the gist of the present invention, it is contemplated that a variety of plants may prove useful for the preparation of purified extracts of photoabsorptive compounds, provided that they are indigenous to arid regions, and more desirably, are located between 35° north latitude and 35° south latitude. Plants pollinating during those months close to or during the solar equinox, e.g. during June or July in the northern hemisphere, would be especially suitable. Palo verde is an exemplary plant of this type, in that it blooms or flowers in early June and is native to the Sonoran ecosystem. This area is characteristic of a particularly sunny and arid climate. In accordance with the discovery of the present invention, it has been found that extracts from this plant are highly photoabsorptive over a broad spectrum of solar radiation and have utility as sunscreen agents. In accordance with the present invention, the photoabsorptive compound(s) can be obtained as extracts from the plants, including plant parts, especially flowering parts including pollen, selected from the group consisting of: the agave, *Agavaceae,* family including such members as: *Yucca elata, Y. breviflora, Agave deserti, A. chrysantha, Dasylirion wheeleri;* the buckwheat, Polygonaceae, family, such as *Eriogonum fasciculatum;* the crowfoot, Ranunculaceae, family, such as *Delphinium scaposum, Anemone tuberosa* and *D. parishii;* the poppy, Papaveraceae, family, including *Platystemon califomicus, Argemone pleiacantha, Corydalis aurea, Eschschoizia californica* and *Ar. corymbosa;* members of the mustard, Cruciferae, family, such as *Dithyrea californica, Streptanthus carinatus* and *Lesquerella gordoni;* members of the legume, Leguminosae, family, such as *Acacia greggii, Prosopis velutina, A. constrica, Senna covesii, Cercidium floridum, C. microphyllum, Lotus huminstratus, Krameria parvifolia, Parkinsonia aculeata, Calliendia eriophylla, Lupinus arizonicus, Olyneya tesota, Astragalus lentiginosus, Psorothamunus spinosus* and *Lupinus sparsiflorus;* members of the loasa family, Loasaceae, including *Mentzelia involucrata, M. pumila* and *Mohavea Confertiflora;* members of the cactus, Cactaceae, family, such as *Carnegiea gigantia, Opuntia leptocaulis, Ferocactus wislizenii, O. bigelovii, O. pheacantha, O. versicolor, O. fulgida, Echinocereus engelmannii, Mammillaria microcarpa, O. basilaris, Stenocereins thurberi, O. violacea, M. tetrancistra, O. ramosissima, O. acanthocarpa, E. pectinatins* and *O. arbuscula;* members of the evening primrose, Onagraceae, family, such as *Oenothera deltoides, Camissonia claviformis* and *Oe. primiveris;* members of the milkweed, Asclepiadaceae, family, including *Asclepias erosa, A. sublata* and *Sarcostemma cynanchoides;* members of the borage, Boraginaceae, family, such as *Cryptantha augusti folia* and *Amsinckia intermedia;* members of the sunflower, Compositae, family, including *Baccharis sarothroides, Monoptiilon belloides, Erieron divergens, Zinnia acerosa, Melampodium leucanthan, Chaenactis fremontii, Calycoseris wrightii, Malacothrix californica, Helianthus annus, H. niveus, Geraea canescens, Hymenothrix wislizenii, Encelia farinosa, Psilostrophe cooperi, Baileya multiradiata, Bebbia juncea, Senecio douglasii, Trixis californica, Machaeranthera tephrodes, Xylorhiza tortifolia, Cirsiinm neomexicanum, Antennaria parviflora* and *Ch. douglasii;* members of the caltrop, Zygophyllaceae, family, including *Larrea tridentata* and *Kallstroemia grandiflora;* members of the mallow, Malvaceae, family, including *Hibiscus coulteri, H. denudatus* and *Sphaeralcea ambigua;* members of the phlox, Polemoniaceae, family, such as *Luanthus aureus;* members of the unicorn plant, Martyniaceae, family, such as *Proboscidiea altheaefolia;* members of the gourd, Cucurbitaceae, family, such as *Cucurbita digitata;* members of the lily, Lilaceae, family, including *Calochortus kennedyi, Dichelostemma pulchellum, Allium macropetalum* and *Hesperocallis indulata;* members of the ocotillo, Fouquieriaceae, family, including *Fouquieria splendens;* members of the figwort, Scrophulariaceae, family, such as *Castilleja sp., Penstemon parryi* and *Orthocarpus purpurascens;* members of the acanthus, Acanthaceae, family, including *Anisacanthus thurberi, Justicia califomica* and *Ruellia nudiflora;* members of the four o'clock, Nyctaginaceae, family, such as *Allionia incarnata, Abronia villosa* and *Mirabilis multiflora;* members of the geranium, Geraniaceae, family, including *Erodium cicutarium;* members of the waterleaf, Hydrophyllaceae, family, such as *Nama demissum, Phacelia bombycina* and *Ph. distans;* members of the bignonia, Bignoniaceae, family, such as *Chilopsis linearis;* members of the vervain, Verbenaceae, family, including *Glandularia gooddugii* and *Verbena neomexicana;* members of the mint, Labiatae, family, such as *Hyptis emoryi* and *Salvia columbariae;* members of the broomrape, Orobanchaceae, family, such as *Orobanche cooperi;* members of the portulaca, Portulaceae, family, such as *Talinum auriantiacum;* members of the carpet-weed, Aizoaceae, family, such as *Sesuvium verrucosum;* members of the flax, Linaceae, family, such as *Linum lewisii;* members of the potato, Solanaceae, family, including *Nicotiana trigonophylla* and *Physalis lobata;* and members of the cochlospermum, Cochlospermaceae, family, such as *Amoreuxia palmatifida.*

Additional plants which may be useful for preparing pollen extracts to provide the photoabsorptive compound(s) of the present invention, include tropical corn hybrids, *Zea mays.*

In order to prepare the various cosmetic formulations of the present invention, such as sunscreens, the extracts of plants, for example, pollen extracts, may be mixed with one or more conventional excipients or vehicles used in the preparation of such cosmetic, especially sunscreen formulations. Various excipients or vehicles may be used to formulate sunscreens for topical application, based upon the plant, especially pollen extracts used as the active ingredient in the formulations. The vehicle utilized may be glycerol or analogues of glycerol, glycols, oil-in-water or water-in-oil emulsions, niosomes, lotions, creams, or ointments. Other vehicles may include, but are not limited to, gels, liposomes, fatty or lipid-based emulsions, sticks, mousses, and aerosols. Additionally, the plant, especially pollen extracts may be formulated in gas-filled lipid bilayer suspensions or foams, such as those described in copending application Ser. No. 08/159,674, filed Nov. 30, 1993, which is incorporated herein by reference in its entirety. Vehicles including oil-in-water emulsions with an acrylate film-forming polymer may be formulated with the plant, especially pollen extracts to provide sunscreens, particularly resistant to water exposure, e.g. to adhere to the skin during activities such as swimming. Lanolin, ceramides, almond oil, peanut oil, and cocoa butter may also be used to formulate such vehicles.

With regard to the sunscreen formulations of the present invention, it is also contemplated that the extracts of plants, especially pollen extracts, may be combined with one or more commercially available sunscreen agents. Such agents may include, but are no means limited to para-amino benzoic acid (PABA) and its esters, salicylates, cinnamates, and benzophenones. PABA esters may include amyldimethyl PABA (Padimate A or Escolol 506) and octyldimethyl PABA (Padimate O or Escolol 507). Salicylates such as octyl salicylate may be used for aiding in the solubilizing of various pollen fractions. Additional salicylates may include but are not limited to homomethyl salicylate (homosalate), 2-ethyl-hexyl salicylate, menthyl salicylate, benzyl salicylate, and benzoyl salicylate. Cinnamates such as cinnamic acid, cinnamaldehyde, cinnamon oils and 2-ethylhexyl-para-methoxycinnamate may also be included in a plant extract, especially pollen extract, based formulation of the present invention. Anthranilates, which are derivatives of ortho-aminobenzoic acid, may also be included in the formulations of the present invention. Typical anthranilates may include menthyl anthranilates and homomenthyl-N-acetyl anthranilate. In addition, benzophenone derivatives such as dioxybenzone, sulisobenzone, and oxybenzone may be incorporated into a given sunscreen formulation.

In addition, physical blocking agents may also be added or mixed in with the plant, especially pollen extract sunscreen formulations for topical delivery to the skin. Such physical blocking or photo-opaque agents may include titanium dioxide, zinc oxide, talc, kaolin, ferric chloride, ichthammol, and a variety of clays. Coloring agents may also be useful as additives to these formulations. These coloring agents may include ferric oxide and any caramelized sugar. Even food grade coloring agents can be utilized.

The efficacy of sunscreen agents is conventionally defined by their sun protection factor (SPF) number. The SPF number is the ratio of the time of ultraviolet exposure necessary to cause erythema with the particular sunscreen on, to the time to erythema without the sunscreen. SPF values vary from 2 (minimal protection) to over 50. The SPF value desired for any sunscreen formulation will obviously depend upon the concentration of the particular photoabsorptive compound of the present invention which is employed. Moreover, the effective concentration of the photoabsorptive compounds of the present invention required to provide protection against skin damage, including erythema or sunburn, caused by solar radiation, will depend largely upon the particular photoabsorptive compound(s) of the present invention which are employed, although the other ingredients used in the sunscreen formulation, and particularly the presence of other commercially available sunscreen agents, will play a role in determining the final result. However, the artisan can determine the required concentration reliably and without considerable effort simply by preparing test formulations with various concentrations of the particular photoabsorptive compound (s), applying these test formulations to the skins of various human subjects, and exposing these subjects to solar radiation for a predetermined period of time, after which, using methods known in the art, the concentration required for a desired degree of protection from solar radiation can be readily calculated.

The present invention also relates to photoabsorptive compound products prepared by the process of extracting said compound(s) from a plant or plant part, wherein said plant is indigenous to an arid region of the world between 35° north latitude and 35° south latitude, and thereafter purifying said compound(s). The step of extracting is carried out using an extracting agent which may be selected from the group consisting of alkanols, especially methanol and ethanol; ketones, especially acetone; ethers, especially anisole; cycloalkanes, especially cyclohexane; alkanes and halogenated alkanes, especially hexane, dichloromethane and chloroform; aromatic hydrocarbons, especially benzene and toluene; and alkoxyalkylated ether polymers, especially methoxymethylated ether polymers such as glyme and diglyme. The methanol may be used with aqueous hydrochloric acid of about 10% (v:v) concentration. Other solvent systems are equally suitable and may be employed, since it is contemplated that any number of different photoabsorptive compounds may be available for extraction, particularly in view of the large number of suitable plants, enumerated further above, from which extracts may be prepared. It may be that these numerous compounds differ significantly in their physical attributes and chemical classifications. It would be expected, consequently, that a variety of solvent systems might be suitable for extracting these compounds. No undue burden is thereby imposed on the artisan, however, since the extraction process can be carried out in a straightforward manner as further described herein, and the efficacy of the extracted compounds for photoabsorption can be determined reliably and quickly using a variable wavelength spectrophotometer. It is thus possible to rapidly and accurately prepare and screen literally hundreds of test extract preparations. All such efficacious extracts are contemplated to be within the scope of the present invention.

The step of extraction is then followed by a step of purification in order to obtain the photoabsorptive compound(s) of the present invention. Standard methods of separation and purification which will be readily apparent to the artisan can be used. Simple filtration is usually sufficient to remove any gross plant debris that may accompany the original extract. Multiple extractions, with intermittent removal of the extraction solvent by evaporation, will serve to isolate and further purify the compound(s) removed from the plant part in the original extraction. Chromatographic techniques of various well-known types can also be used to further separate and purify the photoabsorptive compound (s) of the present invention. The degree of purification needed or desired will depend on the particular photoabsorptive compound(s) involved and the level of photoabsorptive activity which it or they possess. For highly active compounds, extensive purification may not be necessary, provided that the extraction has not also carried with it other contaminating compounds which are found to interfere in some way with the particular end use of the compound which is desired. For example, a contaminating compound may interfere with the preparation of a sunscreen formulation because of some incompatibility with one of the ingredients thereof. On the other hand, the contaminating compound may be found to cause an allergic reaction when applied to the skin of a test animal or human. However, these are matters that are readily determinable by the artisan of ordinary skill, and further purification, where needed, can be carried out without difficulty.

Yet another aspect of the present invention relates to man-made materials protected from damage caused by impinging radiation from about 190 nm to about 500 nm, comprising ultraviolet A, ultraviolet B, and high energy visible light, wherein said materials contain an effective amount of one or more photoabsorptive compounds comprising an extract of a plant or plant part, wherein said plant is indigenous to an arid region of the world between 35° north latitude and 35° south latitude. A class of man-made materials which must be protected from damage caused by solar radiation are various synthetic polymers, since the polymer chains are particularly susceptible to interruption and depolymerization by the photons of solar radiation. The resultant degradation in properties, such as color change, brittleness and cracking, pose a considerable problem in the many areas where synthetic polymers are used and the product is exposed to sunlight on a regular basis. But a few examples are the structural elements used in residential and commercial construction, such as siding and windows wholly or partially fabricated from polymer materials; outdoor advertising displays having components fabricated from polymers; various components of the outer bodies of automobiles fabricated from polymers; and woven materials made from polymer fibers, such as carpeting and drapery fabrics exposed to direct sunlight. Polymers, i.e., synthetic resins are often combined by mixing or lamination with elements such as woven fiberglass or carbon filaments, which considerably increase the structural integrity of the resulting construction. These constructions, for example those used to make the hulls of powerboats and sailboats, as well as some automobile bodies, are exposed to damaging solar radiation and suffer from a deterioration in properties over time, if not properly protected. This protection can be afforded by using the photoabsorptive compounds of the present invention when preparing these constructions. They are most efficiently and reliably used when applying the skim or final coat of synthetic resin, e.g., a polyester, as a component thereof in the desired concentration.

Outdoor synthetic resin coatings, especially paints, which are commonly made from man-made polymers, are especially susceptible to damage from solar radiation because of their inherent exposure to sunlight over long periods of time. Discoloration and cracking are both aesthetically undesirable and pose a threat to the integrity of the underlying structure that is coated and now becomes exposed to the elements.

The effective concentration of the photoabsorptive compounds of the present invention required to provide protection against damage by solar radiation, whether as an additive to a polymer, or to the final polymer coat of a polymer and reinforcing fiber construction, or to a synthetic resin coating or paint, will vary depending upon the photoabsorptive compound(s) used, the particular man-made polymer material or construction, and the degree of exposure to solar radiation involved. However, the artisan can determine the required concentration reliably and without considerable effort simply by preparing test samples or panels with various concentrations of the particular photoabsorptive compound(s), and exposing these test samples or panels to solar radiation for a predetermined period of time, after which, using methods known in the art, the concentration required for a desired degree of protection from solar radiation can be readily calculated.

DESCRIPTION OF PREFERRED EMBODIMENTS

The invention is further demonstrated in the working examples set out further below which represent actual reductions to practice of the present invention. These examples, however, are not intended to in any way limit the scope of the present invention.

In order to confirm the hypothesis concerning the ability of plants in arid regions between 35° north latitude and 35° south latitude to produce photoabsorptive compounds that protect parts thereof, especially the flowering parts including pollen, from solar radiation damage, samples of pollen and flowers were collected from four representative desert plants, mesquite, *Prosopis juliflora;* Mexican palo verde, *Parkinsonia aculeata;* blue palo verde, *Cercidium floridum;* and foothills palo verde, *Cercidium microphyllum.* These plants were selected because they are all diurnally pollinated flowering trees that flower in the spring or summer. Experiments were then performed to determine whether or not photoabsorptive compounds existed in the pollen and flowers and could be removed by extraction.

EXAMPLE 1

Photoabsorptive Compound(s) Obtained from Mesquite, *Prosopis juliflora,* by Hexane/Chloroform Extraction Flowers, pollen and other plant material collected from mesquite, *Prosopis juliflora,* was frozen, then lyophilized in a Labconco Lyph-Lock 12 lyophilizer (Labconco Corp. Kansas City, Mo.) until dry. The lyophilized plant material was removed from the lyophilizer, and subsequently, the stems, leaves, and remaining body of the plants were removed from the pollen. This yielded about 200 mLs of loose, non-green plant material which was largely pollen. Hexane (250 mL) was then added to the pollen material in a volume sufficient to suspend the entire contents. The material did not float, indicating that it was completely lyophilized and that there was no appreciable hydrophobic interaction between the plant material and the hexane. The hexane and pollen mixture was then placed over a cold pack in a polystyrene storage container for temporary storage, and after approximately 48 hours had elapsed, it was decided that sufficient hexane extraction had taken place to proceed. The solvent was then transferred by decanting to a round bottom flask, and an additional 250 ml of hexane was added to the pollen, and the procedure repeated. The hexane fractions were combined, and the hexane was then removed by rotary evaporation on a Büchi RE 121 Rotavapor (Büchi, Switzerland)

The sample of mesquite pollen was allowed to dry and then was resuspended in 250 mL of chloroform (Mallinckrodt, St. Louis, Mo.). The chloroform was allowed to perform extraction on the pollen material for 24 hours as described above, and then removed by rotary evaporation. The mixture was once again suspended in chloroform, filtered with a Whatman No. 1 filter, and the extract concentrated in vacuo to yield the remaining extract.

EXAMPLE 2

Photoabsorptive Compound(s) Obtained from Mesquite, *Prosopis juliflora,* by Acetone Extraction Flowers, pollen and other plant material collected from mesquite, *Prosopis juliflora,* was frozen, then lyophilized and extracted in accordance with the procedures described above in Example 1, except that acetone extraction was performed on the sample of lyophilized mesquite pollen. The fraction was filtered with a Whatman No. 1 filter and then concentrated in vacuo.

EXAMPLE 3

Photoabsorptive Compound(s) Obtained from Mesquite, *Prosopis juliflora,* by Methanol Extraction An additional method of extraction was carried out using the procedures described above in Example 1, by the addition of 250 mL of a 90% methanol, 10% aqueous (v:v) hydrochloric acid (Mallinckrodt Chemicals, St. Louis, Mo.). The mixture was filtered to remove the insoluble plant fiber and pollen, and the extract was concentrated in vacuo. The concentration in vacuo required a water bath to increase the temperature to 50° C.

EXAMPLE 4

Photoabsorptive Compound(s) Obtained from Mexican Palo Verde, *Parkinsonia aculeata;* Blue Palo Verde, *Cercidium*

*floridum;* and Foothills Palo Verde, *Cercidium microphyllum,* by Hexane, Acetone and Methanol Extraction Using the procedures described above in Examples 1 through 3, extraction was carried out on three different species of palo verde, using successively, hexane, acetone and methanol as the extracting solvents.

EXAMPLE 5

Determination of Solar Radiation Absorptivity

UV absorption scans were conducted on the isolated mesquite pollen extracts and on the various isolated palo verde pollen extracts using a Perkin-Elmer Lambda 1110 variable wavelength UV/Visible spectrophotometer (Perkin-Elmer Corporation, Norwalk, Conn., 06859). A reference cuvette with the appropriate extracting solvent was used for the control standard. Each test sample was placed in the sample cuvette and scanned at 5 nm increments from 190 to 600 nm. Extracted fractions were generally diluted 10 to 1,000 fold so as not to saturate the optical density capability of the spectrophotometer. A commercially available sunscreen agent (Bullfrog®, Sun Protection Factor 36, Chatten Inc., Chattanooga, Tenn. 37409) was used as an active control and for comparison of a commercially acceptable solar radiation filtering spectrum. Results of the photoabsorption evaluations are shown in the table of values below, designated Table 1.

TABLE 1

| SAMPLE | EXTRACTION | TISSUE | PEAK ABSORBANCE nm |
|---|---|---|---|
| Bullfrog ® SPF 36 | N.A. | N.A. | 190–328 |
| Mesquite | Hexane | Pollen | 190–250 |
| Mesquite | Chloroform | Pollen | 190–400 |
| Mesquite | Methanol | Pollen | 210–350 |
| Mesquite | Acetone | Pollen | 190–270 |
| Blue Palo V. | Acetone | Pollen | 315–400 |
| Blue Palo V. | Acetone | Flowers | 300–500 |
| Blue Palo V. | Hexane | Pollen | 190–500 |
| Blue Palo V. | Hexane | Flowers | 190–500 |
| Blue Palo V. | Methanol | Pollen | 190–300 |
| Blue Palo V. | Methanol | Flowers | 190–400 |
| Mexican PV | Acetone | Pollen | 190–340 |
| Mexican PV | Acetone | Flowers | 335–485 |

As illustrated in the table of values above, the hexane fractions of the mesquite pollen exhibited strongly absorbing wavelengths indicative of photoabsorptive compounds present in that plant. The chloroform fraction also exhibited significant absorbtion of UV wavelengths, but over a wider spectrum than the hexane extracts, indicating that chloroform was also capable of extracting the desired compound(s) from the mesquite plant. The acetone and the methanol:aqueous HCl fractions yielded strongly UV absorbing components. The mesquite pollen yielded the most interesting photoabsorptive properties with the methanol extract. Not only was there high absorption of UVA, UVB, and UVC, but the amount of compound extracted indicated that the extinction coefficient was either very high, or the amount of excess compound was very concentrated. With regard to the palo verde extractions, of note were the hexane fraction extracts, which possessed the highest absorption properties with a range of strong absorption extending from 190 nm to 540 nm with a lambda ($\lambda$) max of 280–325 nm. The hexane fractions had such high optical density that the samples had to be diluted 1:1,000,000 to achieve an optical density of approximately 1.0 within the lambda ($\lambda$) max range. In comparison, the commercially available Bullfrog® SPF 36 fraction was diluted 1:10. Not knowing the chemical composition or molecular weight of the products being extracted, it is not possible to attribute an extinction coefficient to the active component; however, it is clear that, even if an abnormally large amount of extract (e.g. 250 mg $mL_{-1}$) was solubilized in the aqueous layer, and if the molecular weight was nominal, one would still have a product with a very high extinction coefficient. Interestingly, the Bullfrog® SPF 36 appears to possess a UV cutoff of 390 nm. This absorption property falls short of the upper limits of the UVA range which ends at approximately 400 nm. Furthermore, as discussed previously, in order to fully protect skin from damaging radiation, it is necessary to block absorption well into the visible spectrum. The experiments above demonstrate that the palo verde hexane fraction is clearly effective at blocking the visible spectrum from 400 to 540 nm. These wavelengths of light can penetrate the skin deeply and there interact with porphyrins and dyes to cause subsequent damage to the skin.

What is claimed is:

1. A purified, photoabsorptive plant extract which is prepared by a process comprising (a) extracting a reproductive part of a plant selected from the group consisting of *Prosopis juliflora, Cercidium floridum, Cercidium microphyllum* and *Parkinsonia aculeata* with a non-polar organic solvent;

(b) concentrating said non-polar organic extract from (a) to produce a concentrate which is extracted with a polar, organic solvent; and (c) concentrating said polar organic extract from (b) to produce the purified, photoabsorptive plant extract.

2. A purified extract according to claim 1 wherein said non-polar organic solvent is selected from the group consisting of alkanes, cycloalkanes and aromatic hydrocarbons.

3. A purified extract according to claim 2 wherein said alkane comprises hexane.

4. A purified extract according to claim 1 wherein said polar organic solvent is selected from the group consisting of alkanols, ketones, ethers, halogenated alkanes and alkoxyalkylated ethers.

5. A purified extract according to claim 4 wherein said polar organic solvent is selected from the group consisting of alkanols, ketones and halogenated alkanes.

6. A purified extract according to claim 5 wherein said alkanol comprises methanol.

7. A purified extract according to claim 5 wherein said ketone comprises acetone.

8. A purified extract according to claim 5 wherein said halogenated alkane comprises chloroform.

9. A purified extract according to claim 1 wherein said reproductive part of said plant comprises the flowering part.

10. A purified extract according to claim 9 wherein said flowering part of said plant comprises the pollen.

11. A purified extract according to claim 1 wherein said concentrating steps comprise rotary evaporation.

12. A purified, photoabsorptive plant extract which is prepared by a process comprising (a) extracting a flowering part of a plant selected from the group consisting of *Prosopis juliflora, Cercidium floridum, Cercidium microphyllum* and *Parkinsonia aculeata* with a solvent wherein said solvent is selected from the group consisting of non-polar organic solvents and polar organic solvents;

(b) removing insoluble impurities from said extract of (a); and (c) concentrating said extract from (b) to produce the purified, photoabsorptive plant extract.

13. A purified extract according to claim 12 wherein said non-polar organic solvents and polar organic solvents are selected from the group consisting of alkanols, ketones, alkanes and halogenated alkanes.

14. A purified extract according to claim 12 wherein step (b) comprises filtering said extract.

15. A purified extract according to claim 12 which comprises peak absorbances of from about 190 to about 500 nm.

16. A cosmetic formulation comprising, in combination with a cosmetic excipient, an extract according to claim 12.

17. A cosmetic formulation according to claim 16 which is selected from the group consisting of sunscreens, moisturizing creams and lip balms.

18. A cosmetic formulation according to claim 17 which is a sunscreen.

* * * * *